(12) United States Patent
Fehre et al.

(10) Patent No.: US 7,449,003 B2
(45) Date of Patent: Nov. 11, 2008

(54) BELLOWS FOR COUPLING A SOURCE ACOUSTIC WAVES TO A SUBJECT TO BE TREATED

(75) Inventors: Jens Fehre, Hausen (DE); Bernd Granz, Oberasbach (DE); Christian Meinert, Marloffstein (DE); Ralf Nanke, Spardorf (DE)

(73) Assignee: Siemens Aktiengesellschaft, Munich (DE)

( * ) Notice: Subject to any disclaimer, the term of this patent is extended or adjusted under 35 U.S.C. 154(b) by 852 days.

(21) Appl. No.: 10/458,095

(22) Filed: Jun. 10, 2003

(65) Prior Publication Data

US 2004/0036555 A1 Feb. 26, 2004

(30) Foreign Application Priority Data

Jun. 10, 2002 (DE) .................. 102 25 709

(51) Int. Cl.
*A61H 1/00* (2006.01)
(52) U.S. Cl. .................. 601/2; 601/3; 601/4; 600/437; 600/439
(58) Field of Classification Search ......... 600/437–461; 601/2–4
See application file for complete search history.

(56) References Cited

U.S. PATENT DOCUMENTS

| 4,662,375 | A | * | 5/1987 | Hepp et al. ................. 601/4 |
| 4,674,505 | A | | 6/1987 | Pauli et al. |
| 4,928,672 | A | | 5/1990 | Grasser et al. |
| 5,046,483 | A | * | 9/1991 | Ogura ........................ 601/4 |
| 5,156,144 | A | * | 10/1992 | Iwasaki et al. ............. 601/4 |
| 6,059,741 | A | | 5/2000 | Wess |
| 6,068,596 | A | * | 5/2000 | Weth et al. ............... 600/437 |
| 2001/0046184 | A1 | | 11/2001 | Reitter et al. |

FOREIGN PATENT DOCUMENTS

DE OS33 12 014 10/1984

* cited by examiner

*Primary Examiner*—Brian Casler
*Assistant Examiner*—Sanjay Cattungal
(74) *Attorney, Agent, or Firm*—Schiff Hardin LLP

(57) ABSTRACT

A bellows for coupling a source of acoustic waves having an acoustic propagation medium, to a patient, has a geometrical modification in that region wherein the bellows can be seated against the patient for the introduction of acoustic waves into the patient. The geometrical modification in the propagation path of the acoustic waves generated by the source of acoustic waves shapes the acoustic waves in a designated (designed) manner. Additionally or alternatively, the bellows can have a section in the region that is formed of a different material than the rest of the bellows.

25 Claims, 4 Drawing Sheets

BELLOWS FOR COUPLING A SOURCE ACOUSTIC WAVES TO A SUBJECT TO BE TREATED

BACKGROUND OF THE INVENTION

1. Field of the Invention

The invention is directed to a bellows for coupling a source of acoustic waves, containing an acoustic propagation medium to a living subject.

2. Description of the Prior Art

Acoustic wave sources are employed in medicine, for example, for the disintegration of calculi in the inside of the body of a living subject or for pain therapy. Such a source of acoustic waves can, for example, include an electromagnetic pressure pulse source, an acoustic propagation medium, an acoustic lens or a concave mirror as well as a bellows for coupling the source of acoustic waves to the body of a the subject to be treated. Using the electromagnetic pressure pulse source, pressure pulses are introduced into the acoustic propagation medium, the pressure pulses propagating in the acoustic propagation medium and being focused by the acoustic lens or the concave mirror. The introduction of the focused acoustic waves into the body of the subject ensues via the acoustic propagation medium and the bellows for coupling to the subject.

Conventionally, acoustic waves generated with a source of acoustic waves are not shaped further after passing through the acoustic lens and before entry into the body of the subject. When a surface between the acoustic lens and the body surface of the subject into which the acoustic waves are introduced is considered perpendicular to the main propagation direction of the acoustic waves, one finds that the acoustic waves or the field of acoustic waves is not homogeneously distributed within its −6 dB zone. Instead; zones of very high positive or negative pressure that can lead to negative physical effects on the life form, particularly to irritation of the skin of the subject, are located, for example, close to the middle axis of the source of acoustic waves.

German OS 195 34 809 discloses an apparatus for treating body tissue and for the disintegration of body calculi by means of acoustic energy. In order to avoid undesired deviations from the straight-line propagation of the acoustic waves or from the planned propagation of the acoustic waves upon transition from the apparatus to the body tissue, among the items proposed is to shape the geometry of the boundary surface such that deviations do not ensue, or ensue in controlled fashion. For example, planar, spherical or other boundary surfaces shaped in a controlled fashion can be generated by the pressing force of appropriately shaped applicators.

German OS 33 12 014 discloses an apparatus for the non-contacting disintegration of calculi in the body of a subject using shock waves. The shock waves are coupled into the body of a patient with a coupling member that is preferably elastically deformable. The focus of the shock waves can be set to the treatment region within certain limits by deformation of the coupling member. Disks that are composed of the same material as the coupling members can be additionally attached to the coupling member for expanding the focus adjustment possibilities.

SUMMARY OF THE INVENTION

An object of the present invention is to provide a bellows for coupling a source of acoustic waves, having an acoustic propagation medium, to a living subject such that the negative physical effects on the subject upon the introduction of acoustic waves into the body of the subject are alleviated.

This object is achieved in accordance with the invention by a bellows for coupling a source of acoustic waves having an acoustic propagation medium, to a subject, having a geometrical element that is firmly connected to the bellows and is arranged at that side of the bellows facing away from the subject in that region wherein the bellows can be seated against the subject for the introduction of acoustic waves into the subject, the geometrical element lying in the propagation path of acoustic waves generated with the source of acoustic waves and shaping the acoustic waves in a designated (designed) manner. In accordance with the invention, thus a modified bellows in a source of acoustic waves influences, guides or shapes the acoustic waves generated with the source of acoustic waves in a designed manner after a first shaping by an acoustic lens or a concave mirror, so negative physical effects on the subject to be treated with the acoustic waves, particularly on the skin of the life form, are at least reduced due to the compensation of inhomogeneities of the acoustic field. A good seating of the bellows against the body surface that is pleasant for the patient is assured since the geometrical element is located at the side of the bellows facing away from the life form.

In an embodiment of the invention, the geometrical element is an acoustic mirror. The acoustic mirror can be planar or conical, but at a minimum has two inclined mirror faces, so that the generated acoustic waves or a field of acoustic waves is shaped by partial reflections given passage through the acoustic mirror.

Another shaping of a field of acoustic waves can be achieved in an embodiment of the invention wherein the geometrical element arranged on the bellows has a number of regularly or irregularly arranged objects. A scattering of the field of generated acoustic waves is thereby achieved, as a result of which the field of acoustic waves can be shaped. The objects, for example, can be a field of small cones or a field of objects that have different geometrical shapes and that have a largest dimension that is small compared to the wavelength of the acoustic waves generated with the source of acoustic waves. The largest dimension of the objects in one direction should thereby be approximately one size factor, i.e. about ten times smaller, than the wavelength of the acoustic waves generated with the source of acoustic waves.

In a further embodiment of the invention, the field of acoustic waves can be shaped by an element that acts as acoustic filter that is arranged on the bellows. The acoustic filter can be a high-pass filter or a low-pass filter for the acoustic waves. The element is fashioned of a number of layers with filter effect.

In another embodiment of the invention the element arranged on the bellows is a matter of an acoustic lens or an absorber for acoustic waves, as a result of which the field of acoustic waves generated by the source of acoustic waves can be shaped, so that irritations, particularly occurring at the skin surface of the subject as a consequence of the acoustic waves introduced into the body of the subject, at least can be reduced.

In another embodiment of the invention, the geometrical element arranged on the bellows is fashioned of the same material as the coupling bellows itself. The property of the element as a mirror, a disperser, a filter, a lens or an absorber for the acoustic waves thereby arises as a result of—among other things—the structure or the geometrical shaping of the element.

In another embodiment of the invention, the geometrical element is fashioned of a different material from the bellows, preferably a material that significantly differs in acoustic properties from the acoustic properties of the acoustic propagation medium. Suitable materials for the fashioning of the element are rubber-like materials as well as hard PVC, metal-containing materials as well as, generally, all materials that can be joined well to the material of the bellows, which is usually fashioned of soft PVC, latex or silicone.

The above object also is achieved in a bellows for coupling a source of acoustic waves, having an acoustic propagation medium, to a subject, the bellows having a zone that is geometrically modified in defined fashion at that side of the bellows facing away from the subject in that region wherein the bellows can be seated against the subject for the introduction of acoustic waves into the subject, the geometrically modified zone lying in the propagation path of acoustic waves generated by the source of acoustic waves and shaping the acoustic waves in a designated (designed) manner. This geometrical modification of the bellows is thus a zone of the bellows itself that is geometrically modified in a defined fashion.

In embodiments of the invention, the zone of the bellows can be fashioned such that it has the effect of an acoustic mirror. The zone can be fashioned in the form of a planar or conical acoustic mirror or in the form of an acoustic mirror having at least two inclined mirror faces.

In another embodiment of the invention, the zone of the bellows has a number of regularly or irregularly arranged objects, so that the zone of the bellows has a dispersing effect for acoustic waves. As already described for the attached element, the objects can be small cones or objects that are geometrically shaped in an appropriate manner and that are small, i.e. are at least size factor smaller in their largest dimension than the wavelength of the acoustic waves generated by the source of acoustic waves.

In embodiments of the invention, the zone of the bellows can be fashioned such that it has the effect of an acoustic filter, preferably the effect of an acoustic high-pass filter or an acoustic low-pass filter.

In further embodiments of the invention the zone of the bellows is fashioned such that it has the effect of an acoustic lens or the effect of an absorber for acoustic waves.

The above object also is achieved in accordance with the invention by a bellows for coupling a source of acoustic waves, having an acoustic propagation medium, to a subject, the bellows having a wall section composed of a different material from the rest of the bellows in that region wherein it can be seated against the subject for introducing acoustic waves into the subject, the wall section lying in the propagation path of the acoustic waves generated with the source of acoustic waves and shaping the acoustic waves in a designated (designed) manner.

DESCRIPTION OF THE PREFERRED EMBODIMENTS

Figure 1:
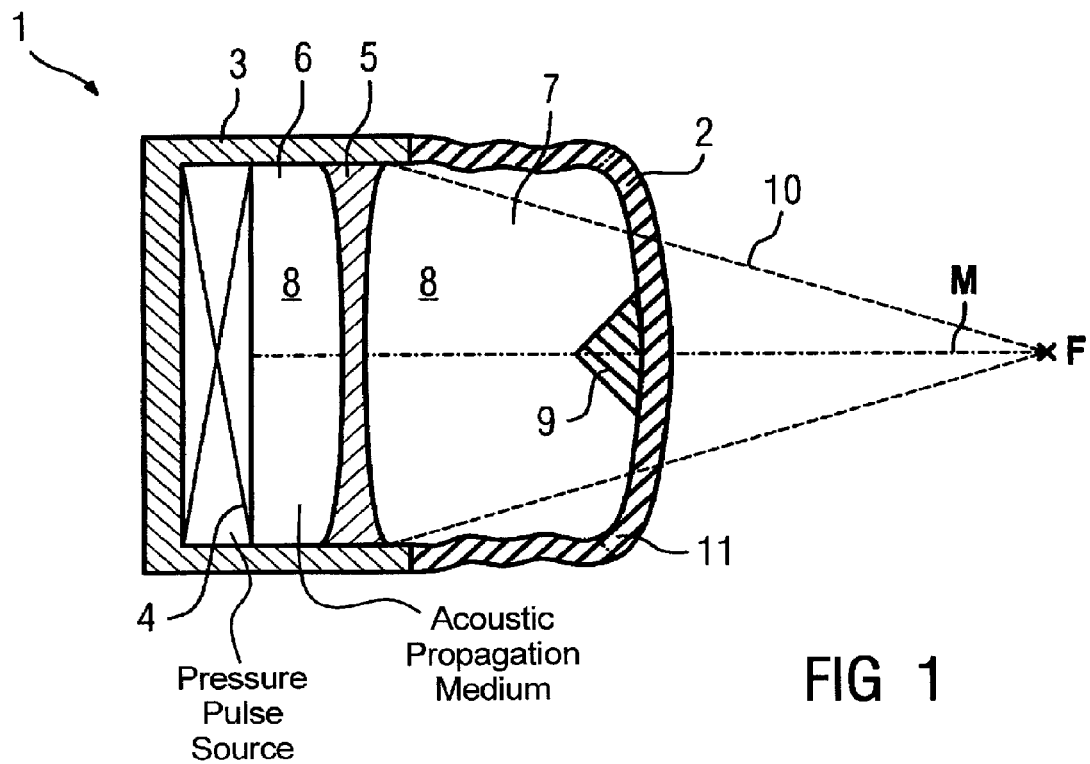
FIGS. 1-12 are sectional views respectively illustrating various embodiments of a bellows for coupling a source of acoustic waves, having an acoustic propagation medium, to a subject, the bellows having a geometrical modification.

FIG. 1 is a schematic illustration, partly in section, of a therapy head 1 for generating acoustic waves that, for example, can be part of a lithotriptor. The therapy head has a housing 3 that is closed at the patient side by a coupling bellows 2, an electromagnetic pressure pulse source 4, a focusing lens 5 and an acoustic propagation medium in the two spaces 6 and 7 contained in the housing 3 in the present exemplary embodiment. In a known way, acoustic waves, particularly shock waves, can be generated with the therapy head 1, whereby the acoustic pressure pulse source 4 introduces pressure pulses into the acoustic propagation medium that intensify into shock waves during their propagation, and are focused with the focusing lens 5 onto a focus zone F disposed substantially on the center axis M of the therapy head. The shock waves are introduced with the coupling bellows 2 into a body (not shown) of a patient against whom the coupling bellows 2 has been seated.

As described above, negative effects on the patient, particularly irritations of the skin of the patient, can occur upon the introduction of the shock waves into the body of the patient due to the inhomogeneity of the generated shock wave field. In order to counter this in a designated manner, the coupling bellows 2 in the exemplary embodiment shown in FIG. 1 has a conical element 9 attached thereto in the region 11 (indicated with dot-dash lines) wherein the coupling bellows can be seated against the patient for introducing shock waves into the patient. The conical element 9 is attached at that side of the coupling bellows 2 facing away from the patient. The conical element 9 has the effect of an acoustic mirror. As can be seen from FIG. 1, the coupling element (acoustic mirror) 9 lies in the propagation path 10 of the acoustic waves indicated with broken lines. After being shaped by the focusing lens 5, the acoustic waves that are generated and propagate in the acoustic propagation medium 8 are shaped again with the coupling element (acoustic mirror) 9 before introduction into the body of the patient, namely by means of partial reflections at the coupling element (acoustic mirror) 9, so that negative effects on the patient, particularly irritations of the skin of the patient, by the acoustic waves can be reduced.

FIGS. 2 through 12 show further coupling bellows that can be arranged at the housing 3 of the therapy head 1 instead of the coupling bellows 2 shown in FIG. 1 and that, like the coupling bellows 2, terminate the therapy head 1 at the patient side. The coupling bellows can be interchanged with one another.

Figure 2:
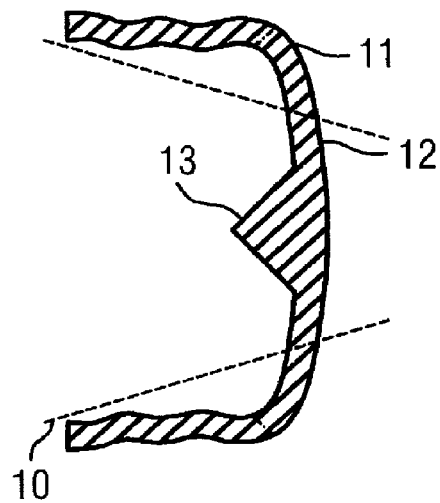

The coupling bellows 12 shown in FIG. 2 differs from the coupling bellows 2 shown in FIG. 1 in that no separately implemented element 9 is attached to the coupling bellows 12; but instead, the coupling bellows 12 itself has a geometrically modified zone 13 at its side facing away from the patient. The zone 13 is conically fashioned and functions as an acoustic mirror. The geometrically modified zone 13 of the coupling bellows 12 is situated in the region 11 (indicated with dot-dash lines) of the coupling bellows that can be seated against the patient for introducing acoustic waves into the body of a patient. Further, the zone 13 is situated in the propagation path 10 of acoustic waves generated with the therapy head 1, so that acoustic waves that are generated and propagate can be shaped again before entry into the body of a patient.

Figure 3:
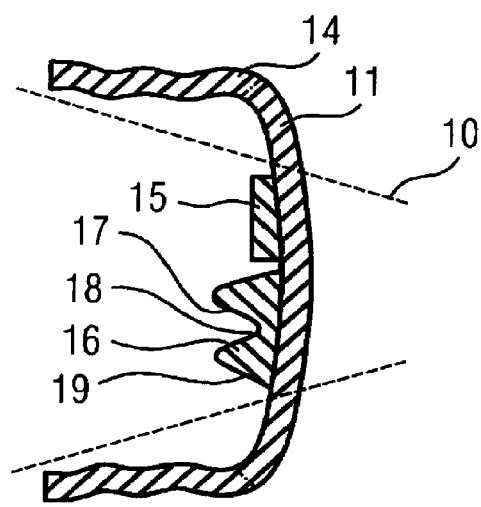
Figure 4:
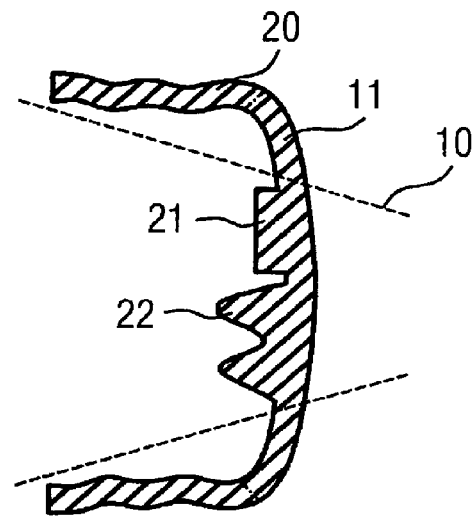

FIG. 3 shows a coupling bellows 14 that has two elements 15 and 16, the element 15 being a planar acoustic mirror, and the element 16 being an acoustic mirror with three inclined mirror faces 17, 18 and 19. After being shaped by the focusing lens 5, the shock wave field is shaped again with the acoustic mirrors 15 and 16 arranged at that side of the coupling bellows facing away from the patient, before entry into the body of the patient in order to avoid negative effects on the patient due to the shock waves. The coupling bellows 20 shown in FIG. 4 differs from the coupling bellows 14 shown in FIG. 3 by virtue of the planar acoustic mirror 21 corresponding to the acoustic mirror 15 and the acoustic mirror 22 corresponding to the acoustic mirror 16 and having three inclined mirror faces, are zones of the coupling bellows 20 itself that can be varied geometrically in a defined way, and are not separately implemented elements arranged on the coupling bellows like the acoustic mirrors 15 and 16.

Figure 5:
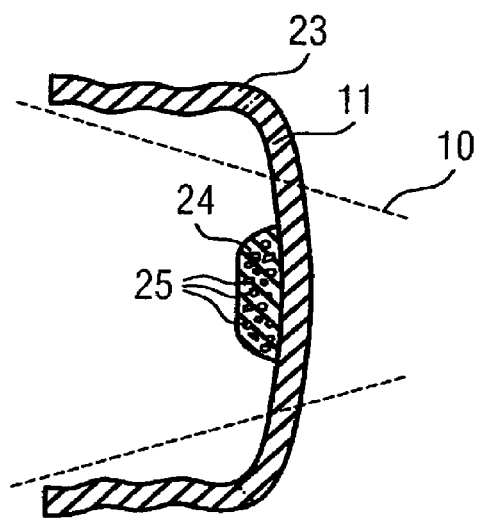
Figure 6:
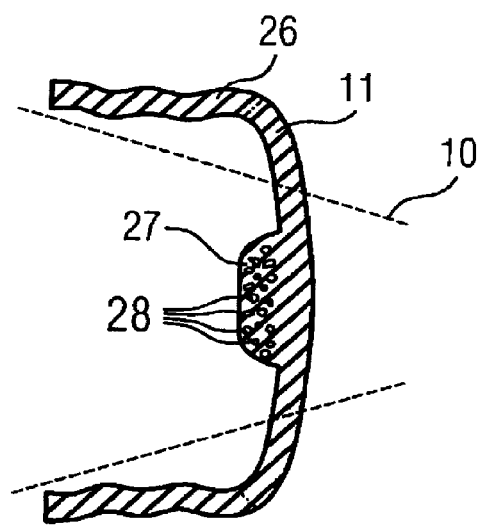

FIG. 5 shows a coupling bellows 23 wherein the side facing away from the patient has an element 24 with a number of regularly or irregularly arranged objects 25. The objects 25 can be small cones or other geometrical objects whose largest dimension is small compared to the wavelength of the acoustic waves generated by the therapy head 1. Preferably, the largest dimension of the objects 25 is at least one size factor smaller than the wavelength of the generated acoustic waves. The objects 25 of the element 24 have a scattering effect on the acoustic waves. Due to the arrangement of the element 24 in the propagation path 10 of the acoustic waves as well as in that region 11 of the coupling bellows 23 that can be seated against the patient for introducing the acoustic waves into a patient, the element 24 thus the functions as a disperser for acoustic waves and thus reshapes the field of the generated acoustic waves before entry into the body of the patient. The coupling bellows 26 shown in FIG. 6 differs from the coupling bellows 23 shown in FIG. 5 by having a zone 27 that is geometrically modified in a defined way that includes a number of regularly or irregularly arranged objects 28 that were introduced into the zone 27. The objects 28 can be small cones or differently shaped geometrical objects. The zone 27 of the coupling bellows 26 provided with the objects 28 has a scattering action on acoustic waves, like the element 24 of the coupling bellows 23.

Figure 7:
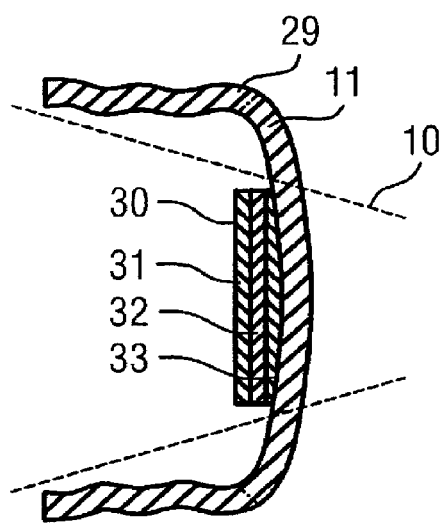
Figure 8:
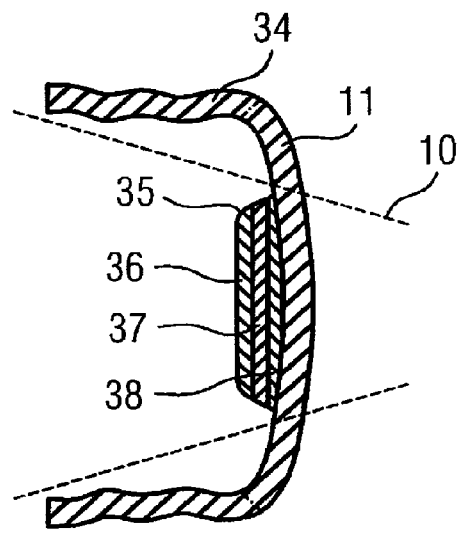

At its side facing away from the patient, the coupling bellows 29 shown in FIG. 7 has an element 30 that is formed as a field of three filter layers 31, 32 and 33 in the exemplary embodiment. The field of acoustic waves is shaped again before entry into the body of the patient by the field of filter layers 31, 32 and 33, which can be low-pass filters or high-pass filters for acoustic waves, for allowing only acoustic waves of a specific frequency to proceed into the body of the patient. The coupling bellows 34 shown in FIG. 8 differs from the coupling bellows 29 shown in FIG. 7 by the coupling bellows 34 itself being geometrically shaped in a defined way, in the region 11 lying in the propagation path 10 of the acoustic waves wherein it can be seated against the patient for introducing acoustic waves into the patient, so that it functions as three acoustic frequency filters 36, 37 and 38.

Figure 9:
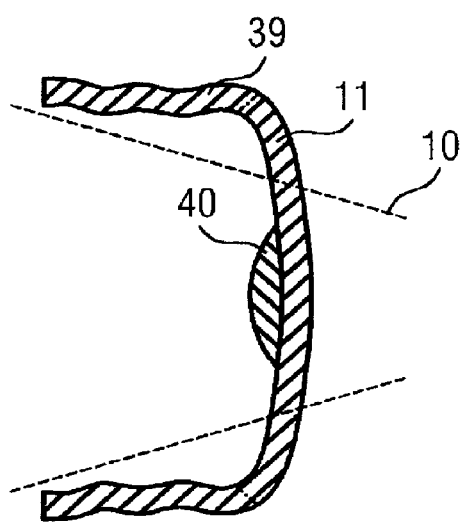
Figure 10:
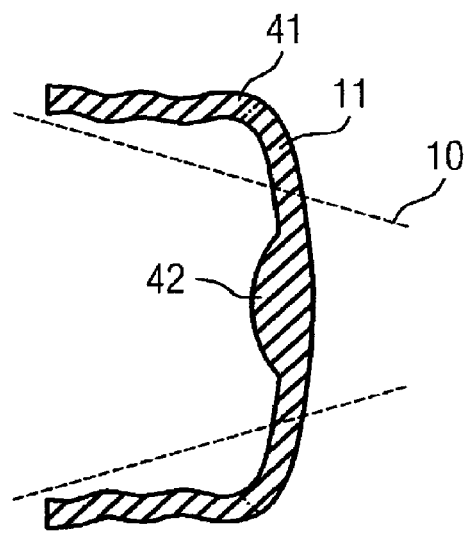

FIG. 9 shows a further coupling bellows 39, which an element functioning as a lens for acoustic waves is arranged at the side thereof facing away from the patient. The lens can be a focusing lens or a defocusing lens that re-shapes the field of acoustic waves generated with the therapy head 1 before entry thereof into the body of the patient. The coupling bellows 41 shown in FIG. 10 differs from the coupling bellows 39 shown in FIG. 9 by having a zone 42 that is geometrically modified in a defined way and develops functions as an acoustic lens. As shown in FIGS. 9 and 10, the function of an acoustic lens can be achieved by the element 40 arranged at the coupling bellows 39 or the zone 42 of the coupling bellows 41 having a convex curvature.

Figure 11:
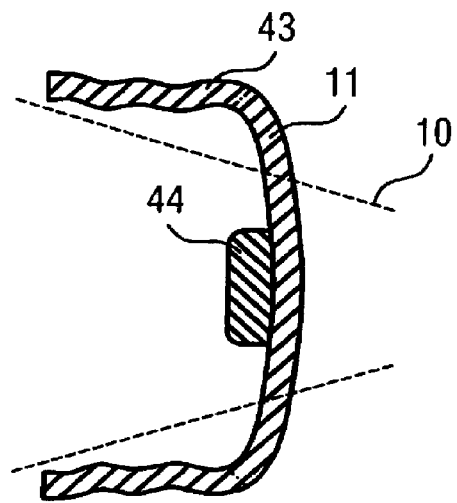
Figure 12:
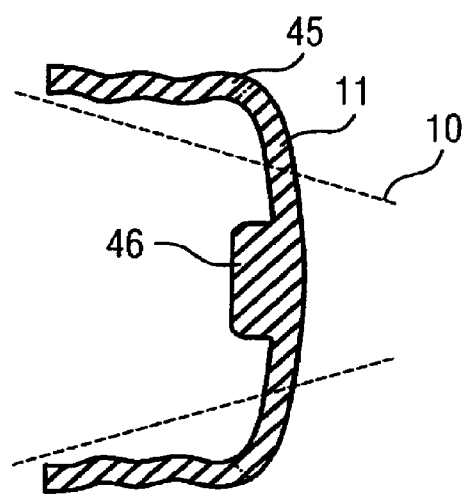

FIG. 11 shows a further coupling bellows 43, with an element 44 that has the effect of an absorber for acoustic waves arranged at the side thereof facing away from the patient. Differing from the coupling bellows 43 shown in FIG. 11, the coupling bellows 45 shown in FIG. 12 itself has a zone 46 that is geometrically modified in a defined way that has the effect of an absorber for acoustic waves.

In the exemplary embodiments shown in FIGS. 1, 3, 5, 7, 9 and 11, the respective elements of the coupling bellows can be formed of the same material as the coupling bellows itself. In the exemplary embodiments of coupling bellows shown in FIGS. 2, 4, 6, 8, 10 and 12, the zones of the coupling bellows are of course fashioned of the same material as the coupling bellows. In the coupling bellows shown in FIGS. 1, 3, 5, 7 and 9, however, the elements can be fashioned from a different material than the coupling bellows, preferably a material that notably differs in terms of its acoustic properties from the properties of the acoustic propagation medium. Coupling bellows usually are formed of soft PVC, latex or silicone. Suitable materials for the elements shown in FIGS. 1, 3, 5, 7 and 9 are likewise rubber-like materials, for example hard rubber, hard PVC, as well as all other materials that can be easily joined to the material of the coupling bellows. For example, the elements of the coupling bellows shown in FIGS. 1, 3, 5, 7, 9 and 11 can be glued on the coupling bellows can be firmly joined to the coupling bellows in some other way. The objects 25 and 28 of the coupling bellows 23 and 26 can, for example, be made of metal.

Figure 13:
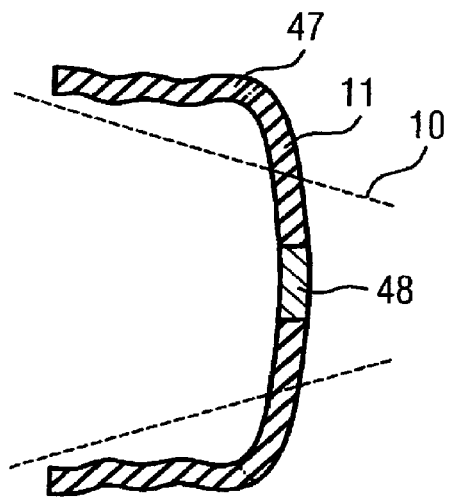
FIGS. 13 and 14 illustrate a bellows having a section formed of a different material than the remainder of the bellows.

FIG. 13 shows another inventive coupling bellows 47 that differs from the coupling bellows already described by the region 11 thereof, at which it can be sated against the patient for introducing acoustic waves into the patient, having a wall section 48 that is fashioned of a different material than the rest of the coupling bellows 47. The material of the wall section 47 likewise can be a rubber-like material such as hard rubber, hard PVC as well as any other materials that can be easily joined to the material of the coupling bellows that, as already mentioned, is usually fashioned of soft PVC, latex or silicone. Accordingly, the field of acoustic waves can be shaped again before entry into the body of a patient dependent on the acoustic properties of the material of the wall section 48.

Figure 14:
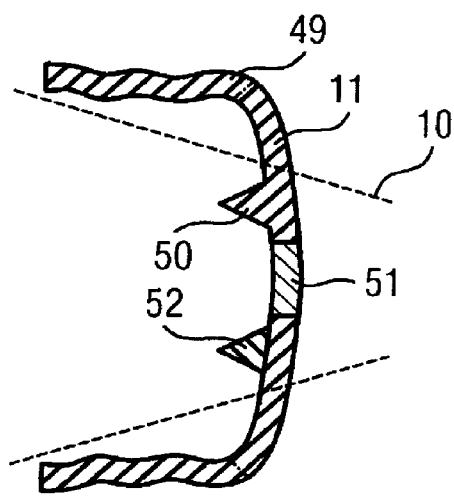

Moreover, mixed forms of the described coupling bellows are possible. Thus, a coupling bellows that itself has one or more geometrically modified zones for shaping a field of acoustic waves can be additionally provided with one or more elements, the zone or element acting as an acoustic mirror, a filter, a disperser, an absorber or a lens. Moreover, such a coupling bellows can additionally have a section that is fashioned of a different material than the rest of the coupling bellows. FIG. 14 shows such a mixed form. The coupling bellows 49 has a conically fashioned zone 50 acting as an acoustic mirror, a section 51 fashioned of a different material than the rest of the coupling bellows 49 and a conical element 52 arranged on the coupling bellows 49 that likewise acts as an acoustic mirror.

The coupling bellows shown in FIGS. 1 through 14 alternatively can be utilized at the therapy head 1 shown in FIG. 1. The coupling bellows are usually easy to interchange and can be economically manufactured, so that the present invention creates the possibility of adapting the shock wave field of a therapy head 1 to the various demands in the therapy by targeted replacement of coupling bellows, and thus to achieve superior gentleness for the patient to be treated. Since the measure respectively undertaken at the coupling bellows—whether arranging a specifically shaped element or a shaping of the coupling bellows itself or by means of a section composed of a different material—interacts with the energy of the shock wave in the focus zone Z roughly as a percentage of area, the change of the energy in the focus zone can be calculated and accordingly the focus zone also can be shaped in a designated manner. The measure undertaken at the coupling bellows usually modifies the focus zone and the disintegration effect of the shock waves—but only slightly. Which of the coupling bellows described in the above examples is employed at a specific therapy head for shaping a field of acoustic waves is dependent on the therapy to be undertaken as well as on the properties of the specific therapy head (that can be measured) in terms of the homogeneity of the field of acoustic waves that can be generated with the therapy head.

The invention is disclosed above with reference to the example of a therapy head with an electromagnetic pressure pulse source, however, the therapy head need not necessarily have an electromagnetic pressure pulse source but alternatively can have some other pressure pulse source, for example a piezoelectric pressure pulse source.

Further, shaping of the shock wave field by a focusing lens need not necessarily have occurred before a shaping of the shock wave field by the element of the coupling bellows or the geometrically modified zone of the coupling bellows or the section of different material in the coupling bellows.

Although modifications and changes may be suggested by those skilled in the art, it is the intention of the inventors to embody within the patent warranted hereon all changes and modifications as reasonably and properly come within the scope of their contribution to the art.

We claim as our invention:

1. A bellows for coupling a source of acoustic waves, containing an acoustic propagation medium, to a treatment patient, said bellows comprising:
   a bellows element configured to be seated against a treatment patient for introducing said acoustic waves into said treatment patient, said bellows element having an exterior and an interior and having an interior side facing away from said treatment patient; and
   a geometric element firmly attached directly to said interior side of said bellows element, said geometrical element being disposed in a propagation path of said acoustic waves and shaping said acoustic waves in a designed manner to provide therapy to the patient.

2. A bellows as claimed in claim 1 wherein said geometrical element comprises an acoustic mirror.

3. A bellows as claimed in claim 2 wherein said acoustic mirror is a planar mirror.

4. A bellows as claimed in claim 2 wherein said acoustic mirror is a conical mirror.

5. A bellows as claimed in claim 2 wherein said acoustic mirror comprises at least two inclined mirror faces.

6. A bellows as claimed in claim 1 wherein said element comprises a plurality of regularly arranged objects.

7. A bellows as claimed in claim 1 wherein said element comprises a plurality of irregularly arranged objects.

8. A bellows as claimed in claim 1 wherein said element comprises an acoustic filter.

9. A bellows as claimed in claim 8 wherein said acoustic filter is a filter selected from the group consisting of high-pass filters and low-pass filters.

10. A bellows as claimed in claim 1 wherein said element comprises an acoustic lens.

11. A bellows as claimed in claim 1 wherein said element comprises an acoustic wave absorber.

12. A bellows as claimed in claim 1 comprising a bellows wall containing said region, said bellows wall and said element being comprised of the same material.

13. A bellows as claimed in claim 1 comprising a bellows wall in which said region is disposed, said bellows wall and said element respectively being comprised of different materials, each of said different materials having acoustic properties that differ from acoustic properties of said acoustic propagation medium.

14. A bellows for coupling a source of acoustic waves, containing an acoustic propagation medium, to a treatment patient, said bellows comprising:
   a bellows wall having a region configured to be seated against a treatment patient for introducing said acoustic waves into said treatment patient, said region having a side facing away from said treatment patient; and
   a zone of said bellows wall at said side in said region disposed in a propagation path of said acoustic waves, said zone having a wave altering shape designed to provide therapy to the patient.

15. A bellows as claimed in claim 14 wherein said zone comprises an acoustic mirror.

16. A bellows as claimed in claim 15 wherein said acoustic mirror is a planar mirror.

17. A bellows as claimed in claim 15 wherein said acoustic mirror is a conical mirror.

18. A bellows as claimed in claim 15 wherein said acoustic mirror comprises at least two inclined mirror faces.

19. A bellows as claimed in claim 14 wherein said zone comprises a plurality of regularly arranged objects.

20. A bellows as claimed in claim 14 wherein said zone comprises a plurality of irregularly arranged objects.

21. A bellows as claimed in claim 14 wherein said zone comprises an acoustic filter.

22. A bellows as claimed in claim 21 wherein said acoustic filter is a filter selected from the group consisting of high-pass filters and low-pass filters.

23. A bellows as claimed in claim 14 wherein said zone comprises an acoustic lens.

24. A bellows as claimed in claim 14 wherein said zone comprises an acoustic wave absorber.

25. A bellows for coupling a source of acoustic waves, containing an acoustic propagation medium, to a treatment patient, said bellows comprising:
   a bellows wall having a region configured to be seated against a treatment patient for introducing said acoustic waves into said treatment patient, said region having a side facing away from said treatment patient; and
   said bellows wall having a wall section in said region composed of a material that is different from a material of a remainder of said bellows wall, said wall section being disposed in a propagation path of said acoustic waves and shaping said acoustic waves in a designed manner to provide therapy to the patient.

* * * * *